United States Patent
Seltzer

[11] 3,943,133
[45] Mar. 9, 1976

[54] S-TRIAZINE HEXACARBOXYLIC ACIDS AND TRIANHYDRIDES

[75] Inventor: Raymond Seltzer, New City, N.Y.

[73] Assignee: Ciba-Geigy Corporation, Ardsley, N.Y.

[22] Filed: Feb. 13, 1975

[21] Appl. No.: 549,632

[52] U.S. Cl. ............................................ 260/248 CS
[51] Int. Cl.² ........................................... C07D 251/24
[58] Field of Search ................................ 260/248 CS

[56] References Cited
UNITED STATES PATENTS 3,843,649   10/1974   Seltzer et al. ................. 260/248

*Primary Examiner*—John M. Ford
*Attorney, Agent, or Firm*—Charles W. Vanecek

[57] ABSTRACT s-Triazine hexacarboxylic acids having the formula

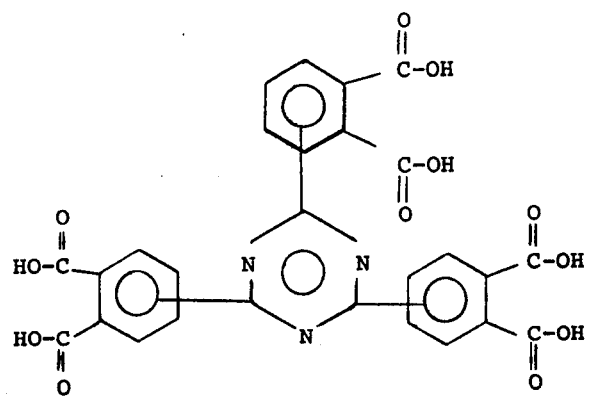

can be prepared by reacting cyanuric chloride with a diakyl substituted aromatic compound and thereafter oxidizing the intermediate to yield the above acid. By dehydrating the acid a corresponding trianhydride is obtained. Such compounds are useful as crosslinking agents for resin systems.

5 Claims, No Drawings

S-TRIAZINE HEXACARBOXYLIC ACIDS AND TRIANHYDRIDES

DETAILED DISCLOSURE

This invention relates to novel s-triazine hexacarboxylic acids and their anhydrides. The acids can be represented by the formula:

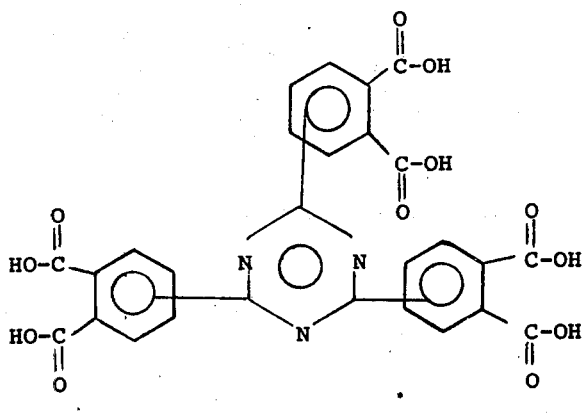

The triahydrides of the invention can be prepared by reacting one mole of cyanuric chloride and three moles of the desired dialkyl substituted aromatic compound, such as ortho-xylene, in the presence of aluminum chloride, to yield an s-triazine derivative which is trisubstituted with dialkyl aromatic groups. The desired tris-(dialkyl aryl)-s-triazine can also be synthesized by trimerizing the corresponding benzonitrile derivative. For example, the trimerization of 3,4-dimethyl benzonitrile will lead to the desired s-triazine intermediate. This intermediate can be oxidized using conventional oxidizing reagents, such as potassium permanganate, to yield the corresponding hexacarboxylic acid compound, which upon heating yields the trianhydride.

The oxidation of the s-triazine intermediate to the hexacarboxylic acid derivative can be accomplished by treating the alkyl derivative with oxidizing agents such as potassium permanganate, chromium oxide, nitric acid, air oxidation or other conventional methods. The hexaacid is dehydrated by conventional methods such as, for example, refluxing in nitrobenzene, refluxing in acetic anhydride or heating the acid in the solid state and removing water by vacuum.

The dialkyl substituted aromatic compounds used in this invention are either well known materials or are readily preparable from known materials by known methods from literature.

The s-triazine trianhydrides of this invention can be used as crosslinking agents for resin systems. Due to their rigid, aromatic structure, these trianhydrides as crosslinking agents contribute to an elevation of the heat distortion temperatures and thermal stabilities of the cured polymers. Thus, the temperature range within which a given resin is useful may be extended through use of these trianhydride curing agents. Furthermore, the trifunctionality of these s-triazine anhydrides makes them especially useful in resin systems where a high degree of crosslinking and/or a rapid cure rate are desirable. Another area of usefulness is in the preparation of thermally stable pigments. Besides posessing the combination of attractive properties outlined above, the trianhydrides of this invention may be prepared from available, rather inexpensive raw materials, a factor which distinguishes them from many prior art trianhydrides.

To illustrate more specifically the invention described above, the following examples are presented.

EXAMPLE 1

Tris-(3,4-Dimethylphenyl)-s-Triazine

A mixture of 36.8 g. (0.20 mole) of cyanuric chloride, 88.0 g. (0.66 mole) of anhydrous aluminum chloride and 250 ml. of o-xylene was heated at 45°C for 1.5 hours. After cooling to room temperature, the mixture was poured into ice water, and then steam distilled to remove the excess o-xylene. The water was decanted from the pot residue and the remaining solid filtered, washed with acetone and dried to yield 58.1 g. of product, m.p. 220°–230°. Recrystallization from benzene gave an analytically pure sample, m.p. 235°–236°.

Anal. Calcd. for $C_{27}H_{27}N_3$: C, 82.50, H, 6.93, N, 10.67. Found: C, 82.55; H, 6.85: N, 10.65.

EXAMPLE 2

Tris-(3,4-Dicarboxyphenyl)-s-Triazine Trianhydride

A mixture of 12.5 g. of tris-(3,4-dimethylphenyl-s-triazine and 250 ml. of pyridine was heated to reflux. About 30 ml. of water and 50 ml. of pyridine were then added to yield a solution. While at reflux 395 g. of potassium permanganate was added in portions over a three-hour period. Additional water was added to keep the reaction mixture fluid. After the addition of potassium permanganate was complete, the reaction mixture was refluxed for 2 hours, then cooled to room temperature and filtered. One-half of the filtrate was concentrated to a white slurry using a Roto Evaporator. The slurry was dissolved in a minimum amount of water and acidified to pH=1 with concentrated HCl. The resulting white precipitate was filtered, washed with water and i-propanol and dried to yield 1.80 g. of the hexacarboxylic acid, m.p. > 500°. The hexacarboxylic acid was heated in refluxing nitrobenzene and filtered. On cooling, the trianhydride crystallized, m.p. 425°–430°. The infrared spectrum (KBr) showed the expected absorption for the anhydride moiety at 5.39μ, 5.61μ.

Anal. Calcd. for $C_{27}H_9N_3O_9$: C, 62.43, H, 1.74; N, 8.09. Found: C, 61.84; H, 1.94, N, 8.36.

What is claimed is:

1. An s-triazine trianhydride having the formula

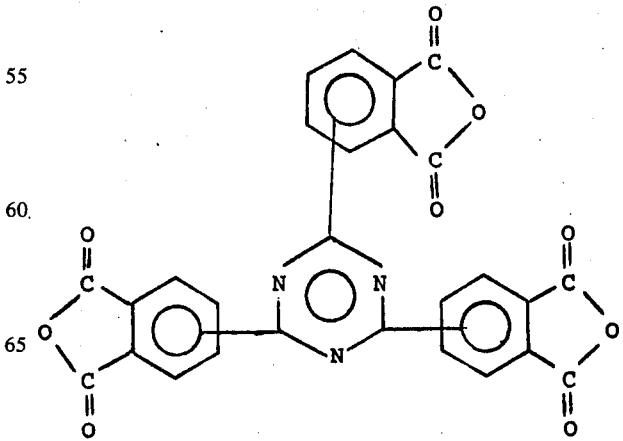

2. The Compound of claim 1 having the formula
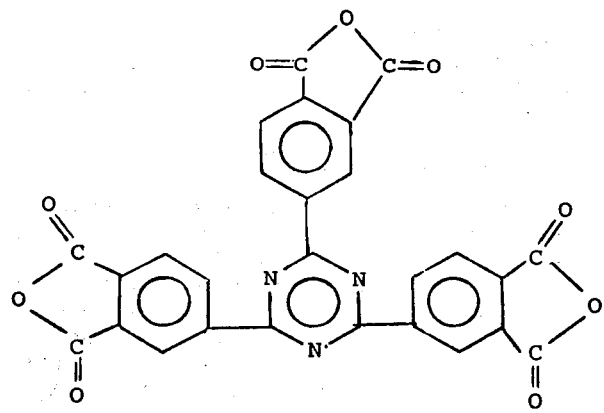
3. An s-triazine hexacarboxylic acid having the formula
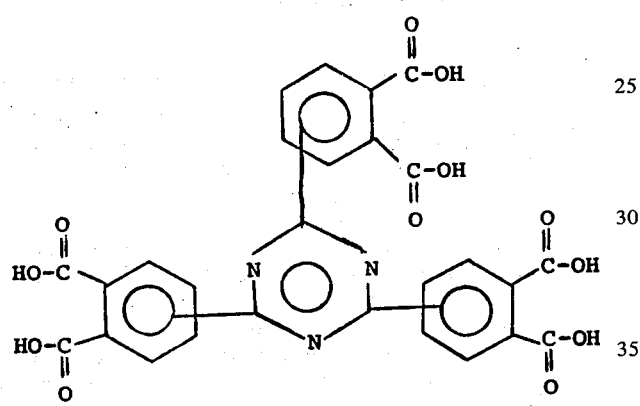
4. The Compound of claim 3 having the formula
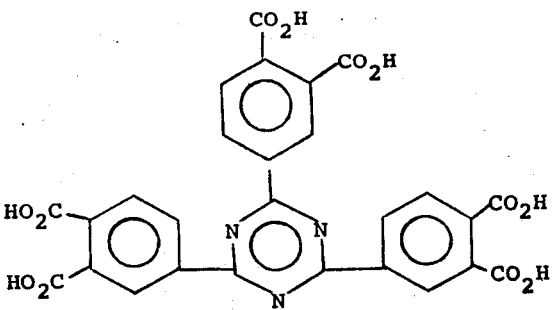
5. A compound of the formula
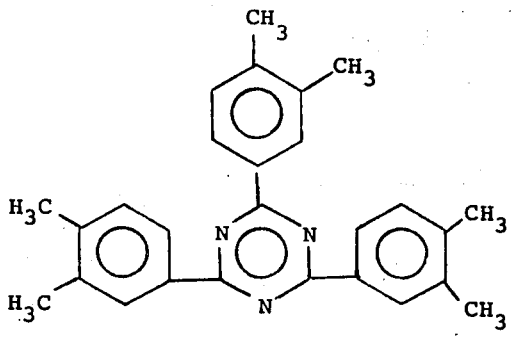
* * * * *